United States Patent [19]

Loesche et al.

[11] Patent Number: 5,223,403

[45] Date of Patent: * Jun. 29, 1993

[54] DEVICE FOR DIAGNOSING PERIODONTAL DISEASE

[75] Inventors: Walter J. Loesche, Ann Arbor; Salam A. Syed, Ypsilanti, both of Mich.; Barbara E. Laughon, Baltimore, Md.

[73] Assignee: University of Michigan, Ann Arbor, Mich.

[*] Notice: The portion of the term of this patent subsequent to May 26, 2009 has been disclaimed.

[21] Appl. No.: 494,277

[22] Filed: Mar. 15, 1990

Related U.S. Application Data

[63] Continuation-in-part of Ser. No. 277,448, Nov. 25, 1988, abandoned, which is a continuation of Ser. No. 740,097, May 31, 1985, abandoned, which is a continuation of Ser. No. 561,245, Jul. 30, 1990, abandoned, which is a continuation of Ser. No. 892,691, May 27, 1992.

[51] Int. Cl.⁵ .......................... C12Q 1/37; C12Q 1/02; C12Q 1/04; C12M 1/34
[52] U.S. Cl. ........................................ 435/23; 435/29; 435/34; 435/291; 435/805
[58] Field of Search ................. 435/23, 24, 28, 29, 435/30, 34, 36, 252.4, 291, 292, 293, 294, 295, 805

[56] References Cited

U.S. PATENT DOCUMENTS

| | | | |
|---|---|---|---|
| 3,985,620 | 10/1976 | Karges | 435/23 |
| 4,175,324 | 11/1979 | Goodson | 424/14 X |
| 4,568,535 | 2/1986 | Loesche | 424/19 |
| 4,603,108 | 7/1986 | Bascomb | 435/34 |

FOREIGN PATENT DOCUMENTS 0165905 12/1985 European Pat. Off. .

OTHER PUBLICATIONS

Laughan, et al., Journal of Clinical Microbiology, Feb. 1982, vol. 15 No. 2, pp. 345-346.
The Research News, vol. 34, No. 2, Mar. 1983, pp. 3-12.

*Primary Examiner*—David M. Naff
*Attorney, Agent, or Firm*—Rohm & Mansanto

[57] ABSTRACT

A colorimetric assay system for diagnosing periodontal disease utilizes a chromogenic test substance for measuring proteolytic activity in a specimen such as subgingival plaque which may contain suspected periodontopathogenic bacteria. The chromogenic test substance comprises a peptide substrate which is hydrolyzable by proteolytic enzymes in the plaque specimen to release a chromophore. Detection of a color change in the test substance indicates whether such proteolytic activity is present. In a specific illustrative embodiment, the chromogenic test substance comprises N-benzoyl-DL-arginine-2-naphthylamide (BANA) or benzoyl-DL-arginine-p-nitroanilide (BAPNA). In the case of BANA, for example, the chromophore, $\beta$-naphthylamide, is detected by the addition of a color developer, such as fast garnet. The development of a red-orange color is interpreted to indicate the presence of periodontal disease associated with anaerobic periodontopathogens, such as *B. gingivalis*, *T. denticola*, and *B. forsythus*, and the development of a yellow color is interpreted to indicate the absence of periodontal disease. The assay method can be carried out with a device having a first region containing on a support carrier a chromogenic test substance hydrolyzable by proteolytic enzymes of periodontopathogenic organisms to release a chromophore and a second region containing on a support carrier a color developer. The first and second regions are arranged so that they can be brought into superposition. The chromophore is released if the periodontopathogenic organisms exceed about $5 \times 10^5$ colony units.

11 Claims, 1 Drawing Sheet

DEVICE FOR DIAGNOSING PERIODONTAL DISEASE

RELATIONSHIP TO OTHER PATENT APPLICATIONS

This application is a continuation-in-part of co-pending U.S. Ser. No. 277,448 filed on Nov. 25, 1988, now abandoned, which was a continuation of U.S. Ser. No. 740,097 filed on May 31, 1985, now abandoned. Ser. No. 740,097 was continued as U.S. Ser. No. 561,245 filed on Jul. 30, 1990, now abandoned, which in turn was continued as U.S. Ser. No. 892,691 filed on May 27, 1992. All of the aforementioned applications were filed in the names of the inventors herein and are assigned to the assignee hereof.

BACKGROUND OF THE INVENTION

This invention relates generally to systems for diagnosing oral diseases in mammals, and more particularly, to a colorimetric diagnostic test for periodontal disease activity in a human being, or an animal.

Periodontal disease is the major affliction of the human dentition. Today, more teeth are lost to the effects of periodontal disease than to caries (tooth decay). Periodontal disease is a group of conditions affecting the gingiva (gum) and the bones that support the teeth. The primary cause of periodontal disease is bacterial plaque which causes an inflammation of the gum which may result in actual destruction of tissue. In some cases, destruction of the bone occurs to the point where teeth lose their attachment thereto.

In periodontal disease, there is usually a large accumulation of bacteria in plaque attached to the tooth, both above (supragingival) and below (subgingival) the gum line. This plaque can become calcified in its depths, forming what is known as calculus. This calculus deposit, and associated plaque, can create a "pocket" between the teeth and the gingiva which is characteristic of the disease. Presently, periodontal disease is diagnosed by clinical observation of indicators such as the presence and depth of pockets, loss of attachment of the teeth to the bone, and papillary bleeding of the gums. Clinical observations, however, are not always reliable indicators. For example, deep pockets are not necessarily infected by bacteria capable of causing inflammatory tissue destruction (periodontopathic bacteria). Unfortunately, there are currently no reliable, inexpensive, and objective means for determining whether or not the pocket is infected with periodontopathic bacteria.

The lack of a diagnostic test has been a serious problem, particularly in view of the severity of the corrective measures typically required to be taken to treat periodontal disease. Such measures can include, the excising of diseased gum tissue so as to expose and debride affected roots and to eliminate pockets. Recently, more conservative surgical treatment has been developed which typically involves detaching a flap of gum from the tooth, cleaning the freshly exposed tooth surface of all calculus and plaque, and then suturing the gingiva back together over the cleaned surface. Both surgical approaches work equally well as long as the patient continues to have professional maintenance treatment.

Although periodontal disease has traditionally been defined as an inflammation of the gums, which means that host tissue is responding to bacteria and/or the products of bacteria, periodontal disease has not been treated like a bacterial infection in the medical sense. For example, periodontal disease had not been treated in the art with antimicrobial drugs because the growth of plaque on the teeth appears to be external to the body, and hence would not seem to be treatable by systemically administered drugs. Moreover, it was not believed that periodontal disease was specific to one, or several, particularly damaging bacteria. In fact, 200 to 300 species of microbes have been isolated from plaque samples. Thus, mechanical treatment which requires instrumenting of the tooth to remove accumulated bacterial deposits non-specifically was deemed to be the appropriate means of treating periodontal disease.

It has been reported that periodontal disease is characterized by a progressive loss of tooth supporting tissue which occurs when the periodontal pocket is colonized by a preponderance of gram negative anaerobic bacteria (see, e.g., Loesche, et al., "Role of Spirochetes in Periodontal Disease," *Host-Parasite Interaction in Periodontal Disease*, Genco and Mergengagen, eds., American Society of Microbiology, Washington, D.C., 1982, pages 62–75 and Slots, "Importance of Black Pigmented Bacteroides in Human Periodontal Disease," Ibid., pages 27–45). Spirochetes and black pigmented bacteroides (BPB) are particularly prominent when pockets bleed upon probing and when there is clinical evidence of disease progression. Thus, the possibility of drug treatment directed towards these anaerobic organisms is raised. In fact, beneficial results have been observed with the use of metronidazole, an antimicrobial effective against anaerobes. Metronidazole is available under the trademark FLAGYL from G. D. Searle & Co., Chicago, Ill. 60680 as well as in generic form from Zenith Laboratories, Inc., Ramsey, N.J. The use of drugs, in the treatment of periodontal disease has accentuated the need for an objective means of detecting the presence of active periodontal infection since some of the clinical symptoms, such as pockets, will still be observable in drug-treated patients, but may not necessarily be infected. Thus, there exists a need in the art for a simple, reliable test for monitoring the efficacy of drug therapy.

Bacteriological diagnosis of elevated levels of spirochetes and BPB by cultural methods can only be done in the research laboratory at the present time. Certain types of the spirochetes, however, cannot be grown in a culture with existing technology.

The spirochetes can be detected and enumerated by microscopic examination using either phase contrast or dark field condensers. One prior art technique used for the diagnosis of periodontal disease involves the microscopic examination of plaque for determination of the presence of motile forms, mostly spirochetes, in order to assess the need for escalating or terminating therapy (see, Keyes, et al., "Diagnosis of Creviculoradicular Infections," Ibid., pages 395–403 and Listgarten, et al., *J. Clin. Periodontal.*, Vol. 8, pages 122–138 (1981). However, no similar microscopic procedure existed for the identification of BPB until the development of highly specific fluorescent antibodies for each of the ten species included within the BPB group. Thus, the dentist/clinician must presently resort to the purchase of expensive microscopes and associated video equipment and/or have sophisticated research laboratory facilities available in order to make necessary assays and measurements for the presence or absence of bacteriological parameters that correlate to periodontal disease.

In view of the present state of the art, there is a great need for a reliable and inexpensive test system for identifying the presence of periodontal disease activity due to anaerobic and/or uncultivatable bacteria. There is additionally a need for a test system which can be performed conveniently by a dentist/clinician. Such a test system would be of significant value in advising a patient of his or her condition, as well as monitoring the effectiveness of treatment.

Accordingly, it is an object of this invention to provide a diagnostic test for determining the presence of periodontal disease due to certain anaerobic bacteria.

It is another object of the invention to provide a diagnostic test system which can identify periodontal disease and which does not require clinical observation so that the disease can be detected at an incipient stage at which it is not yet clinically observable.

It is a further object of the invention to provide a diagnostic test for detecting the presence of, inter alia, *Treponema denticola, Bacteroides gingivalis, Bacteroides forsythus, Capnocytophaga gingivalis* and other organisms in the plaque which possess proteolytic activity, and more specifically the ability to hydrolyze a synthetic trypsin substrate such as N-benzoyl-DL-arginine-2-naphthylamide (BANA).

It is also an object of the invention to provide a diagnostic test for periodontal disease which can be performed in the office of a dentist/clinician by unskilled personnel, and which does not require expensive or special equipment.

It is an additional object of the invention to provide a diagnostic test for periodontal disease which is reliable.

It is yet another of the invention to provide a diagnostic test for periodontal disease which can be used to monitor the virulence of infection.

It is yet a further object of the invention to provide a diagnostic test for periodontal disease which can be performed easily as part of a patient's regular periodic check-up, for epidemiological surveys, for screening examinations, such as military screening, and for monitoring treatment efficacy on periodontal patients.

It is still another object of the invention to provide a diagnostic test for periodontal disease which is capable of detecting anaerobic bacteria under the aerobic conditions of the normal ambience, without requiring the test to be performed in an anaerobic atmosphere.

It is still a further object of the invention to provide a diagnostic test for periodontal disease which does not require culturing of bacterial specimens, and which will test directly a sample of plaque or other such oral specimen.

It is additionally an object of the invention to provide a convenient device which can be used in the diagnosis of periodontal disease.

It is additionally a further object of the invention to provide a colorimetric diagnosis system whereby the presence of periodontal disease is determined by observation of a color change.

SUMMARY OF THE INVENTION

The foregoing and other objects, features, and advantages are achieved by this invention which provides a colorimetric diagnostic test for periodontal disease. The method of diagnosing periodontal disease of the present invention comprises the steps of sampling bacterial flora from the oral cavity of a mammal, illustratively a human being, and then measuring the proteolytic activity of the sample with a chromogenic test substance. In one embodiment of the invention, proteolytic activity is measured by the hydrolysis of BANA since it has been discovered that suspected periodontopathic organisms, such as *T. denticola, B. gingivalis, B. forsythus*, and *C. gingivalis*, are characterized by such activity.

In certain embodiments of the invention, samples of subgingival plaque and gingival crevicular fluid are measured for proteolytic activity by using a chromogenic test substance, which in some embodiments is a peptide substrate, specific to the desired proteolytic enzyme being measured, linked to a chromophore. Of course, one illustrative chromogenic test substance is N-benzoyl-DL-arginine-2-naphthylamide (BANA). A further illustrative example of a suitable chromogenic test substance is benzoyl-DL-arginie-p-nitroanilide (BAPNA). In the case of BANA, for example, an additional color developer, such as an azo-diazo dye like fast garnet, is added to produce a color change responsive to release of the chromophore due to proteolytic activity.

In one specific embodiment of the invention, a sample of subgingival plaque is removed from the oral cavity of a human, incubated in an aqueous solution of a colorless chromogenic test substance, such as BANA, for a period of time sufficient to permit hydrolysis to occur, preferably about a minute to 24 hours. The aqueous solution may contain a buffer, such as a phosphate buffer, so that the pH of the solution is in the range of 5 to 9. In a preferred embodiment of the invention, the pH is approximately 7. The incubating temperature, in this illustrative embodiment, is in the range of approximately 25° C. to 60° C., and preferably 37° C. to 55° C. In the specific illustrative embodiment being described herein, the addition of a drop of fast garnet color developer to a BANA-containing solution will result in the development of a bright orange-red color if periodontal disease associated with the anaerobic bacterial species which hydrolyze BANA is present and a yellow color if periodontal disease is not present.

In still further embodiments of the invention, the color obtained may be either compared to a standardized color chart to indicate the degree of proteolytic activity or measured spectrophotometrically, including densitometrically, or fluorometrically. In another embodiment, sample size can be standardized such that spectrophotometric absorbance thereof will indicate the degree of proteolytic activity quantitatively. In yet another embodiment, the rapidity of color development when a standardized sample size is used will indicate the quantity of *T. denticola, B. gingivalis*, and *B. forsythus* in the plaque sample, thereby giving an indication of the magnitude of the infection in the plaque.

In a device aspect of the invention, the diagnosis of periodontal disease can be aided by the use of a substantially rigid carrier which is provided with a porous portion for absorbing a sample of gingival crevice fluid. The chromogenic test substance, including a chromophore is incorporated into, or chemically bonded to the porous portion of the rigid carrier so that the peptide bond is accessible to proteolytic enzymes present in the sample. The chromogenic test substance is hydrolyzable in response to the presence of periodontopathic components in the sample so as to release the chromophore. In one specific illustrative embodiment, the device is formed as a porous material-coated probe which is configured to fit between a tooth and its associated portion of the gum in the vicinity of the gum line.

In other embodiments, a solid supporting carrier is provided having a first region containing a porous material having the chromogenic test substance incorporated therein and, in some embodiments, a second region is provided on the supporting carrier, or another supporting carrier, which also is provided with a porous material, and has a color developer incorporated therein. In an embodiment where the supporting carrier bears both the first and second regions, they are arranged in spaced relationship to one another so that they can be brought into superposition for combining the color developer with the released chromophore.

BRIEF DESCRIPTION OF THE DRAWING

Comprehension of the invention is facilitated by reading the following detailed description, in conjunction with the annexed single drawing which is a plan view of a diagnostic device embodiment of the present invention.

DETAILED DESCRIPTION OF THE INVENTION

Figure 1:
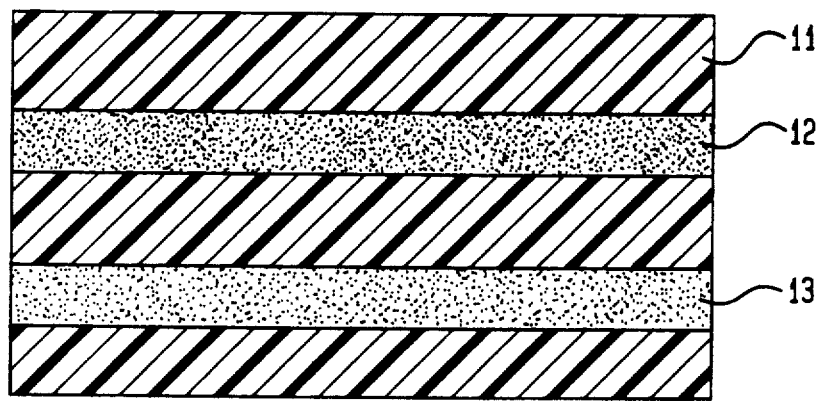

Extensive taxonomic screening of 60 species commonly isolated from subgingival plaque indicates that only *B. gingivalis, B. forsythus*, and the small cultivatable spirochete, *T. denticola*, possess a protease or peptidase which can hydrolyze the synthetic trypsin substrate, BANA. Interestingly, *B. gingivalis* has been recovered in elevated proportions from patients with advanced periodontal disease. Moreover, microscopic analysis has revealed an elevated proportion of spirochetes, such as *T. denticola*, in patients with advanced periodontal disease. Also *B. forsythus* (a non-pigmented Bacteroid) and *B. gingivalis* have been associated with active or acute lesions in periodontal disease. These three BANA hydrolytic organisms have in common that they are associated with periodontal disease and are anaerobic bacteria.

The proteolytic activity was discovered after extensive laboratory tests were performed on cultures of the above-referenced organisms. In particular, the known API ZYM test system, a registered trademark of Analytab Products, Plainview, N.Y., was used for the rapid identification of the various microbial species by their enzyme profile. The enzymatic test, at least under laboratory culturing conditions, has proven to be a reliable means of distinguishing *B. gingivalis* from other BPB which may not be periodontopathic. See Laughon, et al., *J. Clinical Microbiology*, Vol. 15, No. 1, pp. 97-102 (1982) and Laughon, *J. Clinical Microbiology*, Vol. 15, No. 2, pp. 345-346 (1982).

The proteolytic enzyme produced by the suspected periodontopathic organisms is not trypsin because it is not inhibited by trypsin inhibitors, it does not require calcium, it is not inhibited by EDTA, and it is active at acidic pHs. However, it does react with a peptide substrate (e.g., BANA) that is commonly used to measure trypsin, and hence, the enzyme has been termed as "trypsin-like." The presence of this trypsin-like proteolytic or BANA hydrolytic activity may be a significant factor affecting the virulence of these bacteria in periodontal disease. As used herein, the term "proteolytic activity" shall indicate at least protease and peptidase activity. Such proteolytic activity may have a direct effect upon the junctional epithelium in the periodontal pocket, since proteases such as trypsin has been shown to disrupt cell-cell or cell-substratum adhesions in vitro. This protease may also activate latent gingival tissue collagenase by destruction of a collagenase inhibitor present in serum.

As previously indicated, there is a need for a simple, inexpensive diagnostic tool for indicating the presence of periodontal disease due to anaerobic bacteria which a dentist/clinician can use as part of an in-office routine. However, the laboratory culturing and microscopic techniques used in the taxonomic screening, described hereinabove and in the referenced prior art, cannot be accomplished in the office. Surprisingly, it has been discovered that specimens of plaque, for example, contain the requisite amount of organisms to yield a positive enzymatic reaction in the inventive technique described herein, if active periodontal disease exists. In fact, a sample as small as between 10 and 100 micrograms of plaque removed from teeth with bleeding gums or pyorrhea has been shown to yield a positive result. Thus, in accordance with the present invention, a method of detecting or demonstrating elevated levels of *B. gingivalis, T. denticola*, or *B. forsythus*, in a plaque sample, gingival fluid, tissue biopsy, or similar oral specimen, can be equated to a positive diagnosis of active periodontitis due to anaerobic bacteria. This invention therefore enables a clinician to advise a patient of the presence of the disease and to commence a course of treatment which will reduce or suppress these anaerobic organisms in the plaque. Additionally, the invention provides a simple system for monitoring the efficacy of therapeutic treatment.

As discussed, the most frequently implicated periodontopathic organisms as determined by cultural and microscopic procedures are gram negative anaerobic bacteria, such as *B. gingivalis, B. forsythus*, and *T. denticola*. These three species produce a proteolytic enzyme which hydrolyses BANA in vitro. Measurement of the level of the same proteolytic activity toward BANA in the bacterial plaque specimen can be used to diagnose active periodontal disease due to anaerobic bacteria. In a preferred embodiment, proteolytic activity is measured with a chromogenic test substance which is hydrolyzed by the enzyme to release a chromophore which may be visually observed or made visible by addition of a color developer. Such a colorimetric assay is simple, inexpensive, and can be performed by a dentist/clinician without requiring a high level of skill, an extended period of time, or expensive and complex equipment.

In a preferred embodiment of the present invention, an oral specimen removed from the vicinity of teeth exhibiting clinical characteristics of periodontal disease is incubated with a colorless peptide substrate specific to the suspected enzyme. *B. gingivalis, B. forsythus*, and *T. denticola* produce a proteolytic enzyme which is capable of hydrolyzing the colorless peptide substrate, thereby releasing a chromophore as a reaction product. This released chromophore can then be colorimetrically observed by the addition of another chromogenic agent, or color developer. The presence or absence of color is correlated and corresponds to the presence or absence of elevated bacterial conditions related to active periodontal disease.

In a specific illustrative embodiment of the invention, the colorless peptide substrate is N-benzoyl-DL-arginine-2-naphthyl-amide (BANA). Upon incubation with proteolytic enzyme (s) in the specimen, the chromophore $\beta$-naphthylamide, is released from its linkage with the carboxyl group of arginine. The subsequent addition of a color developer, such as fast garnet, results in the formation of a bright orange-red color if there is a high level of enzymatic activity in the specimen. The development of a yellow color is interpreted as a negative result. Of course, there are variations of colors in between yellow and orange-red which can be interpreted as varying degrees of enzymatic activity, and therefore as indicative of a condition which should be monitored by the dentist/clinician.

In an alternative advantageous embodiment, the peptide substrate is N-benzoyl-DL-arginine-p-nitroanilide (BAPNA) which forms a color as it hydrolyses, thereby obviating the need for an additional color developer. The absence of the formation of color indicates the lack of periodontal disease activity and the formation of a yellow color indicates the presence of elevated levels of periodontopathic bacteria.

It is to be understood, however, that other chromogenic test substances can be used in the practice of the invention. Since trypsin and trypsin-like enzymes attack proteins and peptides at arginine or lysine residues, it is apparent that other chromophore-containing peptides involving these basic amino acids, could be substituted for BANA or BAPNA. Illustrative examples are the stereoisomeric analogues of the BANA and BAPNA compounds described hereinabove, such as L-BANA and L-BAPNA. $T.$ $denticola$ and some $B.$ $gingivalis$ strains are active in vitro against L-pyrrolidonyl-$\beta$-naphthylamide (PNA), so that this non-peptide chromophore may also be of value in the diagnosis of anaerobic periodontal infections. All chromogenic test substances, mentioned herein, can be purchased from chemical supply houses such as Sigma, St. Louis, Mo. As used herein, the term "chromogenic test substance" designates any composition which, when subjected to the proteolytic activity of periodontopathic bacteria will produce a visual indicator thereof.

In a specific illustrative embodiment, samples of plaque are removed from the oral cavity of a test subject with a sterile curette and suspended in an aqueous solution by vigorous agitation in a small, stoppered pre-sterilized vial. A stock solution of BANA is prepared by dissolving 44 mg BANA (Sigma Chemical Company, St. Louis, Mo.) in 1 ml dimethyl sulfoxide (DMSO). Prior to use, the BANA stock solution is diluted with a 1:100 by volume mixture of 0.1M Tris (hydroxymethyl) aminomethane hydrochloride buffer at pH 8.5. The buffered BANA solution was added to the plaque sample and allowed to incubate either at room temperature or 37° C. overnight. The addition of a drop of fast garnet produced a color, within about 30 seconds.

Laboratory results indicate that the pH of the liquid BANA-sample solution can range from between about 5.0 and 9.0, preferably from about 7 to 8.5. Other buffers, such as Sorenson phosphate buffer or a phosphate buffer with EDTA, can be used. The results show that a non-buffered solution in pure distilled water works as well as a buffered solution. In some embodiments, however, a non-aqueous, but physiologically acceptable suspending medium which does not interfere with the desired enzymatic activity of the specimen can be used. Incubation generally requires a period of time sufficient to permit hydrolytic action to occur, which in practical embodiments ranges from a fraction of an hour (on the order of about 1–30 minutes) to about 24 hours. Moreover, the incubation temperature should be in the range of about 25° C. to 60° C., and preferably between approximately 37° C. to 55° C.

Diagnostic test results can be obtained more rapidly by increasing the incubation temperature to increase the rate of hydrolysis. A test which may require an overnight incubation period at 37° C. will yeild a result in approximately 15 minutes at 55° C. Although the normal physiological temperature is about 37° C., it has been discovered that the enzymes which yield positive results in the inventive diagnostic test system, surprisingly, are not denatured at temperatures considerably higher than the physiological temperature. In fact, accurate results can be obtained even at temperatures which are in excess of 60° C., as illustrated in TABLE I below. TABLE I shows the effect of incubation temperature on hydrolytic reaction with BANA in the buffered test solution described herein by pure cultures of the referenced organisms. If temperature does not affect their proteolytic activity, $B.$ $gingivalis$ and $T.$ $denticola$ should give a positive test result. $B.$ $intermedius$ and $S.$ $mutans$, which should exhibit a negative test result at any temperature, are included for comparative purposes. The results indicated hereinbelow demonstrate that higher incubation temperatures will not affect test accuracy.

TABLE I

| Species | 37° C. | 50° C. | 60° C. | 70° C. | 80° C. |
|---|---|---|---|---|---|
| B. gingivalis | +(6/6)* | +(6/6) | +(6/6) | +(5/5) | +(4/4) |
| T. denticola | +(4/4) | +(4/4) | +(4/4) | +(2/2) | +(2/2) |
| B. intermedius | −(4/4) | −(4/4) | −(4/4) | −(2/2) | −(2/2) |
| S. mutans | −(2/2) | −(2/2) | −(2/2) | −(1/1) | −(1/1) |

*number of times positive or negative over number of times tested.

With respect to the color developer, it should be noted that other developers will demonstrate colorimetrically the release of a chromophore and can be utilized in the practice of the invention. Illustrative examples include the azo-diazo dyes, fast garnet-gbc salt (Sigma Chemicals, St. Louis, Mo.) chemically designated o-amino-azotoluene-diazonium salt; fast blue; and fast black. An acidified solution of p-dimethylaminocinnamaldehyde is yet another example of a color developer which can be used in the practice of the invention. In fact, p-dimethylaminocinnamaldehyde gives better color differentiation between a positive and a negative result since a positive result with this color developer is reddish purple in contrast to yellow for a negative result.

In an alternative embodiment, proteolytic activity can be measured with a chromogenic test substances which includes a fluorophore, such as 2-arginine-7-amino-4-trifluoromethyl coumarin derivatives. The combination of a peptide substrate with a fluorophore will result in the production of a color change in response to proteolytic action of the specimen which is observable as fluorescence under UV light upon release of the fluorophore. Observable will be the Stokes shift from fluorescent blue to green, for example. Therefore, the term "chromophore" as used herein should be interpreted broadly to include a substance which absorbs visual or ultraviolet light or which fluoresces.

Experience indicates that interpretation of the degree of color development in the diagnostic test system of the present invention is readily amenable to the development of standardized colors charts for comparison purposes to determine the presence or absence of enzymatic activity, or bacterial activity. Although the test has been described herein, primarily as a qualitative yes/no/maybe test, it is to be understood that the test may be made quantitative with sample quantity standardization. Thus, spectrophotometric measurement of color absorbance, illustratively at 405 nm for BANA with fast garnet color developer, and the application of Beer's law, would enable quantitative analysis.

Advantageously, the relative rapidity of color development, when a standard sample size is used, is an indication of the quantity of *T. denticola, B. gingivalis*, and *B. forsythus* in a subgingival plaque sample, and hence, the magnitude of the anaerobic periodontal infection. For example, a plaque sample which gives a positive color change after 5 minutes of incubation with the chromogenic test substance at a given temperature has more *T. denticola, B. gingivalis*, and *B. forsythus* than a plaque sample which gives a positive color change after one hour or 24 hours of incubation. Measuring the length of time required for the production of a positive test result will, thus, yield information concerning the level of periodontopathic disease activity and/or efficacy of treatment of periodontal disease.

In the implementation of the above-described specific embodiment of the instant invention, the sampling technique included the removal of subgingival plaque with a curette. It should be appreciated that, in principle, the sampling techniques contemplated as being effective for the purposes of this invention can be any such method as is known in the art and can be applied to sample and tissue, fluid, or other specimen suspected of being diseased, and therefore includes, by way of example, subgingival plaque, gingival crevicular fluid, supragingival plaque, oral tissue, saliva or oral rinse expectorant, etc. Saliva or oral rinse expectorants, of course, could be concentrated prior to use by any known means. Preferably, the suspected periodontally-diseased specimen would be removed from either the most periodontally involved site per quadrant in patients with clinically observable signs of periodontal disease or from the mesial buccal proximal site of each first molar on patients without any obvious signs of periodontal disease. Preferably, the supragingival plaque at the sample site would be removed and discarded when the specimen comprises primarily subgingival plaque. Filter paper, or the like, can be placed in the orifice of a gingival crevice to collect gingival crevicular fluid by capillary action. The protein is then eluted off of the filter paper and subjected to the chromogenic test substance, in some embodiments. In other embodiments, the filter paper itself can be subjected to the chromogenic test substance.

In accordance with a further aspect of the invention, various device embodiments for facilitating diagnosis of periodontal disease by the colorimetric assay procedure of the present invention can be devised and made available either individually or as part of a kit. Although the foregoing illustrative examples were directed toward an embodiment wherein the proteolytic activity of an oral specimen was measured in a liquid solution containing the specimen and a chromogenic test substance, the proteolytic activity of the specimen could be measured by numerous alternative embodiments in accordance with the principles of the invention.

In a contemplated device embodiment, a substantially rigid carrier is provided with at least one porous surface portion to absorb or receive an oral specimen and/or chromogenic test substance, and in some embodiments, a color developer.

In one specific illustrative device embodiment, the substantially rigid carrier is a porous material-coated probe. The probe and the porous portion is configured, for example, to fit into the orifice of a gingival crevice. Insertion of the probe causes gingival fluid to be absorbed into the porous portion and for the subgingival plaque to be adsorbed to the surface. In one specific embodiment, the probe is further provided with a chromogenic test substance chemically bound to or otherwise incorporated into the absorbent porous surface portion. Alternatively, the chromogenic test substance can be applied to the probe subsequent to collection of the gingival fluid, plaque, or other oral specimen, illustratively by application of the chromogenic test substance to the porous probe surface or by immersion of the probe in a liquid solution of the chromogenic test substance. The probe, with the specimen, is permitted to incubate in the presence of the chromogenic test substance for a period of time sufficient to permit hydrolysis, and thereby to release the chromophore, if proteolytic activity is present in the sample. Subsequently, the probe may be subjected to a color developer, if necessary.

In still a further embodiment, gingival crevicular fluid, for example, may be collected on a porous solid support material such as Periopaper, a cellulose paper which is obtainable from Harco, Tustin, Calif. Advantageously, the amount of fluid sample collected on Periopaper can be measured with a galvanometer, such as a Periotron, also available from Harco, Tustin, Calif. Thus, sample size may be quantified and an estimation of magnitude of the anaerobic infection may be facilitated.

Referring to the figure, another device embodiment 10 is shown wherein a solid carrier structure 11, which may illustratively comprise plastic or cardboard, is provided with a first region 12 comprising, in one embodiment, a porous material, such as filter paper, impregnated with a chromogenic test substance. Carrier structure 11 is further provided with a second region 13 comprising a porous material impregnated with a second reagent, which in some embodiments may be a color developer. First and second regions 12 and 13 may be in spaced relationship to one another so that they can be brought into superposition with one another by simply folding the first region back onto the second region. In certain embodiments, first and second regions may be deposited on the carrier structure as a film or laminated or adhered thereto as a separate layer. In alternative embodiments, multiple carrier structures may be provided for supporting or incorporating one or more of the specimen, chromogenic test substance, or color developer. Illustrative porous materials useful in the practice of the invention, include, without limitation, fibrous materials such as paper and woven or non-woven fabrics. These materials may be (a) natural polymeric carbohydrates and their synthetically modified, cross-linked or substituted derivatives including cellulose and cellulose esters; (b) natural polymers including proteins and their derivatives; (c) natural hydrocarbon polymers such as latexes and rubbers; (d) synthetic polymers which can be prepared with suitably porous structures, such as nylon; (e) inorganic materials which can be prepared in suitably porous form or which can be used as fillers in one of the above polymeric materials; or (f) mixtures or copolymers of the above. As indicated, the porous material may comprise the solid support or may be deposited on, or otherwise applied to, a non-porous carrier, such as the aforementioned rigid probe structure. Of course, embodiments may be devised wherein the chromogenic test substance is incorporated into a gel, or other matrix structure, such as polyacrylamide gel or agar.

Any chromogenic test substance, of the type described hereinabove which is subject to hydrolysis by proteolytic activity of periodontopathic bacteria to release a chromophore, may be employed in the practice of the device embodiment of this invention. In a practical embodiment, the chromogenic test substance is prepared as a liquid solution for absorption into or deposition onto the porous or absorbent material by any technique known in the art, such as dipping or spray-coating. The chromogenic test substance-impregnated material then dried. In a specific embodiment, a stock solution of BANA is prepared by dissolving 44 mg BANA in 1 ml DMSO as described hereinabove. The BANA stock solution is diluted with a buffer (typically from 1:50-1:1000 by volume mixture) having a pH in the range of 5-9. In specific advantageous embodiments, the buffer comprises 0.1M Tris (hydroxymethyl) aminomethane hydrochloride at pH 8.5. Of course, the stock solution may also contain any stabilizers, preservatives, or additives as are known in the art and necessary or desirable for inclusion in the solution.

Likewise, if a color developer is necessary in order to obtain a visual indication of the released chromophore from a given chromogenic test substance, any known color developer, such as the azo-diazo dyes mentioned hereinabove, may be employed in the practice of the device embodiment of the invention. A solution of the color developer (illustratively about 0.1%), buffered in the range of pH 5-9, and any desired stabilizers, preservatives, or other additives can be prepared. In some embodiments, the color developer solution is absorbed or otherwise deposited onto, or bound to, porous material comprising a solid support or carrier, or affixed to a carrier structure, and then dried. In other embodiments, the liquid color developing solution may be applied directly to the chromogenic test substance-containing portion.

In a use embodiment of the device shown in the figure, a plaque sample was removed from a site using a curette and deposited directly onto first region 12 which is a BANA-impregnated strip of filter paper. Second region 13 is a color developer-impregnated strip of filter paper, illustratively an azo-diazo dye color developer such as fast blue or fast garnet.

Carrier 11 is folded so that first and second regions 12 and 13 are brought into superposition and close contact with each other. The carrier, including first and second regions 12 and 13, may be immersed in water or a liquid buffer solution, for example, or otherwise wetted so that the dried reagents thereon are activated. The first and second regions are maintained in contact so that proteolytic activity of the specimen can hydrolyze the chromogenic test substance and the released chromophore can couple with the color developer. In the specific BANA embodiment, naphthylamide released by action of proteases in the oral specimen will produce an observable color when it reacts with the color developer to indicate the presence of anaerobic infection associated with *B. gingivalis, T. denticola*, and *B. forsythus*, either individually or in combination.

In some embodiments, the whole device assembly 10 may be inserted into a heating block to increase the rate of hydrolysis for a predetermined time, illustratively about 1-15 minutes, at about 55° C.

Laboratory test results have demonstrated that increasing color intensity can be associated with increasing numbers of bacteria. A weak positive test result corresponds to about $5 \times 10^5$ colony forming units (CFU) of *B. gingivalis* and 1 to $2 \times 10^6$ CFU of *T. denticola*; whereas, strong positive test result is associated with $5 \times 10^6$ CFU of *B. gingivalis* and 1 to $2 \times 10^7$ CFU of *T. denticola*.

In one embodiment for demonstrating the efficacy of the colorimetric assay method of the present invention in diagnosing periodontal disease, approximately 400 samples of subgingival plaque were collected and analyzed. The specimens were taken from patients with advanced clinical disease and from diabetic children and adults (a high risk group for periodontal disease) and from ostensibly healthy adults. Thus, both positive and negative results were expected. Samples of subgingival plaque were removed with a curette and placed in about 0.4 ml of distilled water.

The plaque specimens thus obtained were (1) subjected to the BANA test procedure described hereinabove; (2) examined microscopically for spirochetes (*T. denticola* can not be quantitatively cultivated and therefore its presence in the plaque sample was estimated indirectly by counting spirochetes); and (3) cultured and examined for *B. gingivalis*. Each patient from which a specimen was collected was also examined for clinical symptoms of periodontal disease, such as papillary bleeding, pocket depth, and loss of attachment of the tooth to the bone.

Some of the results are shown in TABLE II hereinbelow which shows the relationship between the BANA test results, percent spirochetes in the specimen, and number of bacteria and spirochetes per high power field (hpf). For the microscopic examination, 10 microliters of dispersed sample were placed on a glass slide under a 20×30 mm cover slip and sealed. It should be noted that the specimens for the microscopic examination were kept in an anaerobic chamber until use. The microscopic examination was performed with a Zeiss dark-field microscope. Twenty microscopic fields as visualized by the 100X oil immersion objective lens, or 200 bacteria, whichever came first, were counted. The bacteria were characterized as follows: spirochetes (small, medium, or large), fusiforms, selenomonads, motile rods, sessile rods, and cocci. Both percentages and actual numbers of each type were calculated. The volume of one high power field is approximately $1.86 \times 10^{-6}$ ml. In this analysis *T. denticola* would appear as a small spirochete.

TABLE II

| RELATIONSHIP BETWEEN COLOR REACTION AND MICROSCOPIC COUNT OF SPIROCHETES | | | | |
|---|---|---|---|---|
| | COLOR REACTION | | | |
| | Positive | Quest. | Negative | Significance |
| bacteria/hpf | 21 | 12.5 | 6.1 | p <.0001 |
| spirochetes/hpf | 9.0 | 3.0 | 0.6 | p <.0001 |
| % spirochetes | 43 | 22 | 8.1 | p <.0001 |
| No. of Plaques | 157 | 52 | 188 | Total 397 |

Table II reveals that the plaque samples which gave a positive color response (red) in the BANA test of the instant invention, exhibited an average of 43 percent spirochetes, 9.0 spirochetes per high power field, and 21 bacteria per high power field. An orange color response was counted as "questionable" and indicated a proportion of spirochetes and level of spirochetes that was intermediate between the valves in the positive and negative plaques. Plaque samples which gave a negative response (yellow) in the BANA test contained an average of 8.1 percent spirochetes, 0.6 spirochetes per high power field, and 6.1 bacteria per high power field. These results are significantly different from each other. Thus, color development in the BANA test is both a function of the proportion of spirochetes and the total number of spirochetes in the plaque sample.

TABLE III shows the relationship between the BANA test results (color reaction) and the number of various size spirochetes per high power field.

TABLE III

RELATIONSHIP BETWEEN COLOR DEVELOPMENT AND NUMBER OF SPIROCHETES PER HIGH POWER MICROSCOPIC FIELD (hpf)

| Color Reaction | Total | Spirochetes/hpf | | |
|---|---|---|---|---|
| | | Small | Inter. | Large |
| Positive (165) | 9 | 5.3 | 2.3 | 1.3 |
| Questionable (53) | 3 | 1.8 | 0.9 | 0.3 |
| Negative (188) | 0.6 | 0.5 | 0.07 | 0.01 |

Referring to TABLE III, when the BANA test resulted in a positive reaction, there were 9 spirochetes per high power field as compared to 3 spirochetes per high power field when the results were questionable and 0.5 spirochetes per high power field when the results were negative. Thus, when few or no spirochetes were seen on the high power field, the BANA test produced a negative result. These results indicate that the small spirochetes, such as $T.$ $denticola$, accounted for most of the spirochetes in the positive reactions. Subsequent studies using highly specific antibodies to $T.$ $denticola$ have shown that $T.$ $denticola$ contributes significantly to the BANA reactions in the plaque.

TABLE IV shows the relationship between the BANA color reaction test results and the pocket depth measurements on 290 of the sampled pockets. The positive and questionable colorimetric results correlated with average pocket depths of 6.8 mm and 6.7 mm, respectively. In comparison, a negative result in the colorimetric test correlated with an average pocket depth of 4.5 mm. Clinically, pocket depths of greater than or equal to 6 mm are considered to be indicative of periodontal disease. Thus, the BANA test corresponds and correlates with a generally accepted clinical standard for periodontal disease.

TABLE IV

RELATIONSHIP BETWEEN COLOR REACTION AND POCKET DEPTH

| Color Reaction | No. of Sites | Pocket Depth |
|---|---|---|
| Positive | 115 | 6.8 mm |
| Questionable | 31 | 6.7 mm |
| Negative | 144 | 4.5 mm |

More recently, immunological assays and DNA probes have been devised for detecting the presence of suspected periodontopathogenic organisms. However, these assays are so specific that they detect only the complimentary species. Since it appears that more than one species of microorganism are implicated as periodontal pathogens, multiple assays would be required to clearly indicate the presence or absence of disease, thereby increasing the cost and complexity associated with the use of these techniques. Thus, one would need at least three immunological assays to detect $B.$ $gingivalis$, $T.$ $denticola$, and $B.$ $forsythus$, and three DNA probes to detect these organisms. None of these assays are simple, economic chair-side procedures.

Laboratory and clinical results have demonstrated that the accuracy of the BANA test of the present invention is between about 85–90%. The term "accuracy" as defined as the number of plaque samples which are positive for both spirochetes by immunological assays and BANA hydrolysis (true positive) plus the number of plaque samples which are negative for both spirochetes and BANA hydrolysis (true negative) divided by the total number of samples. Accuracy values for DNA probes for $B.$ $gingivalis$, $B.$ $intermedius$, and $A.$ $actinomycetemcomitans$ are reported to range from 44 to 74% (Savitt, et al., $J.$ $Periodontol.$, Vol. 59, pp. 431–438, 1988); whereas accuracy values for monoclonal antibodies for $B.$ $gingivalis$ are reported to be about 70% accurate (Zambon, et al., $J.$ $Periodontal.$, Vol. 56 (11 Suppl.), pp. 32–40, 1985). These findings indicate that the BANA hydrolysis test of the present invention is a simple and accurate indicator of periodontal disease and compares favorably with the more expensive DNA probes and immunological reagents.

A clinical study was conducted to evaluate the specificity and the sensitivity of BANA hydrolysis compared to the detection of $T.$ $denticola$ and $B.$ $gingivalis$ by an immunological technique; specifically by highly specific polyclonal antibodies in an enzyme linked immunosorbant assay (ELISA). This technique is described by Bretz, et al., Benzoyl-arginine naphthylamide (BANA) hydrolysis by $Treponema$ $denticola$ and/or $Bacteroides$ $gingivalis$ in periodontal plaques, $Oral$ $Microbiol.$ $Immunol.$, in press.

The antibodies to $T.$ $denticola$ and $B.$ $gingivalis$ detected about $10^4$ to $10^5$ colony forming units (CFU) of these organisms, whereas the detection limits for these organisms by the BANA hydrolysis test of the present invention is between $5 \times 10^5$ and $5 \times 10^6$ CFU.

A comparison of various diagnostic methodologies with respect to detection limits is summarized below in TABLE V.

TABLE V

| Method | Detection Limit | % of Plaque Flora* |
|---|---|---|
| Cultural | $10^2$ | 0.001% |
| DNA Probes | $10^3$ to $10^5$ | 0.001% to 0.10% |
| ELISA | $10^4$ to $10^5$ | 0.01% to 0.1% |
| BANA | $10^5$ to $10^6$ | 0.1% to 1.0% |
| Microscopic Exam | $10^5$ to $10^6$ | 0.1% to 1.0% |

*Assuming that 1 mg wet weight of plaque is present in a pocket that is 6 mm or more deep and that 1 mg contains $10^8$ cfu.

The ELISA test is sensitive enough to detect colonization by specific periodontopathic organism, however, the BANA test detects a threshold level of periodontopathic organisms which, according to the results of clinical studies, is a more valuable tool for diagnosing the clinically diseased state. As shown in TABLE V, the BANA test for the presence of spirochetes and motile organisms has a detection limit of about $10^5$ CFU. This test is not likely to yield a positive result unless the BANA positive organisms and the spirochetes comprise more than about 0.5 to 1% of the plaque in the pocket. Of course, as also shown at TABLE IV, the correlation of the BANA test with the clinical observation of periodontal disease is excellent. The cultural procedures, the DNA probes, and the ELISA assays will detect fewer organisms and are likely to be positive when the sought after organisms are present at levels that are not associated with clinical disease. The use of these procedures therefore results in a high number of false positive results.

The advantages and benefits associated with the use of the colorimetric diagnostic test for periodontal disease according to the present invention are considered to be numerous and commercially significant. The diagnostic methods are useful in periodontal therapy as well as initial diagnosis of the presence or absence of an anaerobic infection. It is believed that the present invention is particularly useful in identifying common periodontitis, namely chronic destructive periodontitis, wherein the patient or specific tooth sites displays significant increases in *B. gingivalis, T. denticola*, and *B. forsythus*, and other heretofore unidentified BANA positive organisms in the plaque samples. The diagnostic test is also helpful for quantitative evaluation of various stages of treatment of the disease and can aid in a determination of whether treatment has been adequate and whether additional modalities of treatment are warranted. The method is particularly suited for use at periodic maintenance visits to determine whether retreatment is necessary.

It should further be appreciated that for purposes of this invention, the diagnostic test is not limited to human periodontal disease, but can be equally applied to the diagnosis of the disease in mammals in general. As such, the methods of the present invention will find application in the veterinarian sciences.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A device for diagnosing periodontal disease, said device comprising:
    at least one supporting carrier;
    a first region on the at least one supporting carrier, the first region comprising a porous material having a chromogenic test substance incorporated therein, the chromogenic test substance being hydrolyzable by proteolytic enzymes in periodontopathogenic organisms to release a chromophore; and
    a second region on the at least one supporting carrier comprising a porous material having a color developer incorporated therein, said first and second regions being in spaced relationship to one another so that they can be brought into superposition, whereby said chromophore is released if the periodontopathogenic organisms exceeds about $5 \times 10^5$ colony forming units of periodontopathogenic organisms.

2. The device of claim 1 wherein the chromogenic test substance is a peptide substrate containing arginine and/or lysine residues which is specific to an enzyme which acts on a substrate for trypsin activity combined with a chromophore.

3. The device of claim 2 wherein the substrate is a peptide substrate and is selected from the group consisting of N-benzoyl-DL-arginine-2-naphthylamide or N-benzoyl-DL-arginine-p-nitroanilide.

4. The device of claim 2 wherein the substrate is L-pyrrolidonyl-$\beta$-naphthylamide.

5. The device of claim 1 wherein the color developer is an azo-diazo dye.

6. The device of claim 5 wherein the azo-diazo dye is selected from the group consisting of fast garnet, fast blue, or fast black.

7. The device of claim 1 wherein said porous portion comprises absorbent fibrous, woven or nonwoven porous material selected from the group consisting of natural polymeric carbohydrates and natural hydrocarbon polymers.

8. The device of claim 1 wherein there is further provided heating means adapted to receive the supporting carrier.

9. The device of claim 8 wherein said heating means comprises a dry heat incubator for heating the supporting carrier to temperatures between about 45° and 60° C.

10. The device of claim 1 wherein said porous portion comprises absorbent fibrous, woven or nonwoven porous materials selected from the group consisting of synthetic polymers and synthetically modified, cross-linked or substituted derivatives of natural polymers.

11. The device of claim 1 wherein said porous portion comprises absorbent fibrous, woven or non-woven porous natural polymer material.

* * * * *